(12) United States Patent
Lanois et al.

(10) Patent No.: US 9,220,497 B1
(45) Date of Patent: Dec. 29, 2015

(54) SUTURE PASSER

(71) Applicant: VALERIS MEDICAL, LLC, Marietta, GA (US)

(72) Inventors: Daniel Brian Lanois, Atlanta, GA (US); C. Grey Friend, Roswell, GA (US)

(73) Assignee: Valeris Medical, LLC, Marietta, GA (US)

( * ) Notice: Subject to any disclaimer, the term of this patent is extended or adjusted under 35 U.S.C. 154(b) by 0 days.

(21) Appl. No.: 14/744,134

(22) Filed: Jun. 19, 2015

(51) Int. Cl.
*A61B 17/04* (2006.01)
*A61B 17/062* (2006.01)
*A61B 17/00* (2006.01)

(52) U.S. Cl.
CPC ......... *A61B 17/0469* (2013.01); *A61B 17/0625* (2013.01); *A61B 17/00234* (2013.01); *A61B 17/0482* (2013.01); *A61B 17/0485* (2013.01); *A61B 2017/0023* (2013.01); *A61B 2017/00349* (2013.01); *A61B 2017/047* (2013.01)

(58) Field of Classification Search
CPC ........... A61B 17/0469; A61B 17/0625; A61B 17/00234; A61B 17/0485; A61B 17/0482; A61B 17/0483; A61B 17/062; A61B 2017/2932; A61B 2017/2926; A61B 2017/047; A61B 2017/0023; A61B 2017/00349

See application file for complete search history.

(56) References Cited

U.S. PATENT DOCUMENTS

| | | | |
|---|---|---|---|
| 5,147,373 A | 9/1992 | Ferzli | |
| 7,166,116 B2 | 1/2007 | Lizardi et al. | |
| 7,758,597 B1 | 7/2010 | Tran et al. | |
| 7,922,744 B2 | 4/2011 | Morris et al. | |
| 8,057,489 B2 | 11/2011 | Stone et al. | |
| 2003/0065337 A1* | 4/2003 | Topper | A61B 17/0469 606/144 |
| 2010/0130990 A1 | 5/2010 | Saliman | |
| 2011/0251626 A1 | 10/2011 | Wyman et al. | |
| 2012/0116422 A1* | 5/2012 | Triplett | A61B 17/0469 606/144 |
| 2014/0155914 A1 | 6/2014 | Schneider | |

* cited by examiner

*Primary Examiner* — Jocelin Tanner
(74) *Attorney, Agent, or Firm* — Davis L. King

(57) ABSTRACT

A suture passer device for creating a suture loop in tissue has a handle having a fixed handle portion and a movable handle portion, a tubular shaft with a proximal and a distal end for capturing a suture, and a needle attached to the movable handle and positioned internal of the fixed handle and the tubular shaft. When the movable handle closes the needle is passed through a distal opening transverse to the tubular shaft. The needle has an end to hold a suture and form a loop in the tissue.

10 Claims, 19 Drawing Sheets

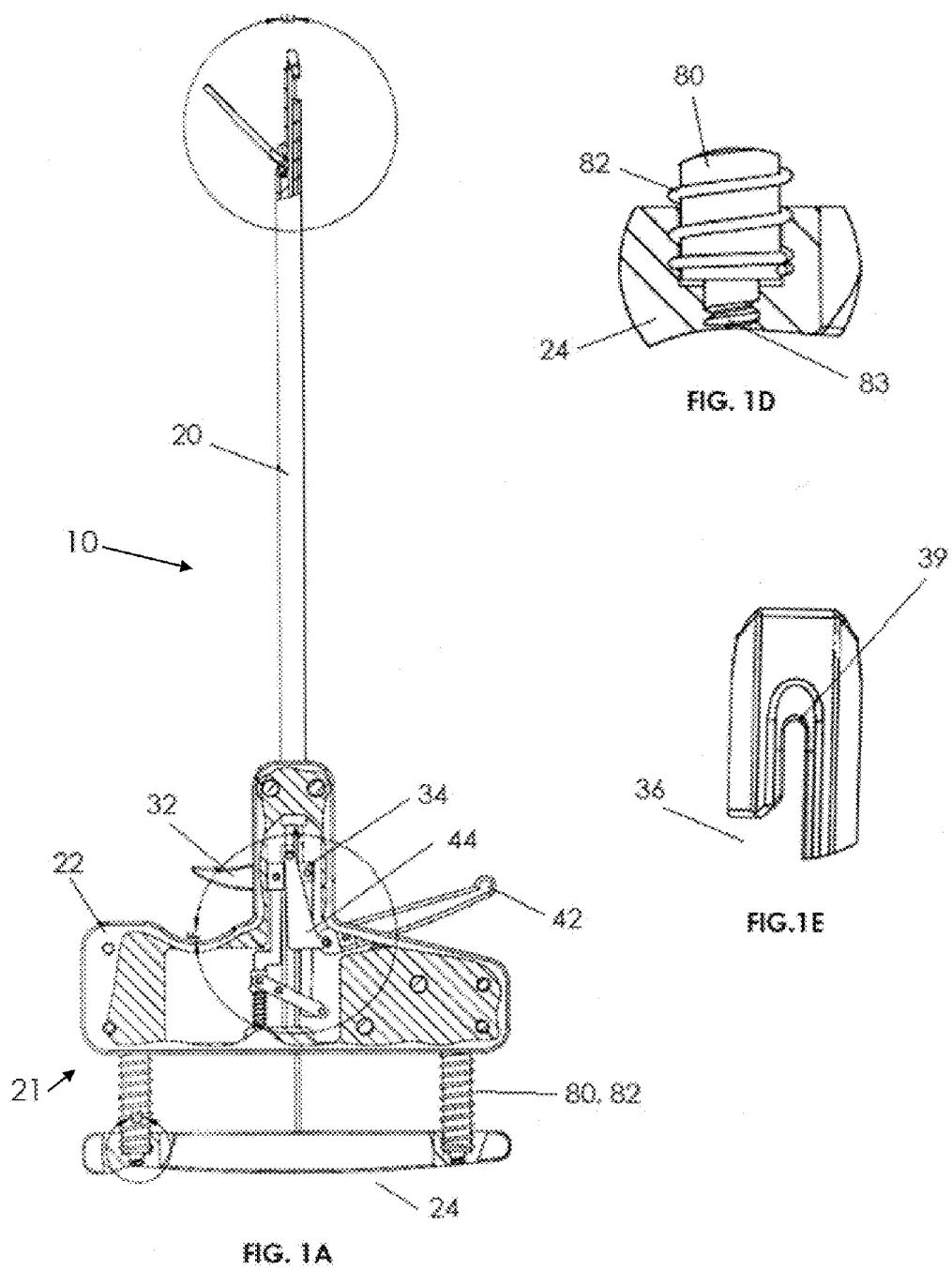

SUTURE PASSER

TECHNICAL FIELD

The present invention relates to devices and methods to pass a suture through material such as, for example, body tissues of a surgical patient and in particular for passing sutures in an orthopedic surgical procedure.

BACKGROUND OF THE INVENTION

Various conditions affecting a patient may require surgical intervention involving passing a suture for example to repair a tear, repair an incision, pass grafts, attach grafts and anchor implants. Various suture passers have been proposed. There is a need for an improved suture passer.

SUMMARY OF THE INVENTION

A suture passer device for creating a suture loop in tissue has a handle having a fixed handle portion and a movable handle portion, a tubular shaft with a proximal and a distal end for capturing a suture, and a needle attached to the movable handle and positioned internal of the fixed handle and the tubular shaft. When the movable handle closes the needle is passed through a distal opening transverse to the tubular shaft. The needle has an end to hold a suture and form a loop in the tissue.

The suture passer device also has a movable jaw clamp, movable from an open position to a closed clamping position and a retractable hook movable longitudinally along the length of the tubular shaft at the distal end.

The handle further has a first trigger mechanism connected to the movable jaw clamp by a linkage, wherein activation by retraction of the first trigger mechanism moves the movable jaw clamp to a closed clamping position. The jaw clamp including the distal opening. It also has a second trigger mechanism connected to the retractable hook by a linkage, wherein activation by retraction of the second trigger mechanism extends the retractable hook external of the tubular shaft to allow capturing a suture in an opening of the retractable hook.

A method of creating one or more suture loops in tissue comprises the steps of: a) providing a suture passer device having a handle assembly, the handle assembly having a first trigger mechanism, a second trigger mechanism and a movable proximal handle portion attached to a fixed handle portion biased to an open position by one or more springs; a tubular shaft; a movable jaw clamp, movable from an open to a closed clamping position by the activation of the first trigger mechanism; a retractable hook movable by activation of the second trigger mechanism; a suture passer needle connected to the movable proximal handle and stowed inside the tubular shaft; b) extending the retractable hook by activating the second trigger mechanism; capturing a suture in an opening or slot of the extended retractable hook; c) retracting the retractable hook; d) clamping the movable jaw clamp to position tissue between the captured suture and the movable jaw clamp by activation of the first trigger mechanism; and e) compressing the movable handle portion to move the needle through an opening in the movable jaw clamp as an end of the needle holds the suture and the needle is bent directionally transverse to the tubular shaft and the end penetrates through the tissue past the closed movable jaw clamp to form a suture loop.

BRIEF DESCRIPTION OF THE DRAWINGS

The invention will be described by way of example and with reference to the accompanying drawings in which:

FIG. 1A is a plan view of the suture passer shown partially in cross-section at the handle end and the tip end of the device.

FIG. 1D is a view of a portion of the handle attachment taken from FIG. 1A.

FIG. 1E is an enlarged view of the suture hook with the slotted opening with a groove for holding the suture.

FIG. 7A is an enlarged view of the tip end taken from FIG. 7.

FIG. 8A is an enlarged view of the tip end taken from FIG. 8.

FIG. 9A is an enlarged view of the tip end embedded in tissue taken from FIG. 9.

FIG. 10A is an enlarged view of the tip end with projecting needle taken from FIG. 10.

FIG. 11A is an enlarged view of the tip end with the retracted needle taken from FIG. 11.

DETAILED DESCRIPTION OF THE INVENTION

Figure 1:
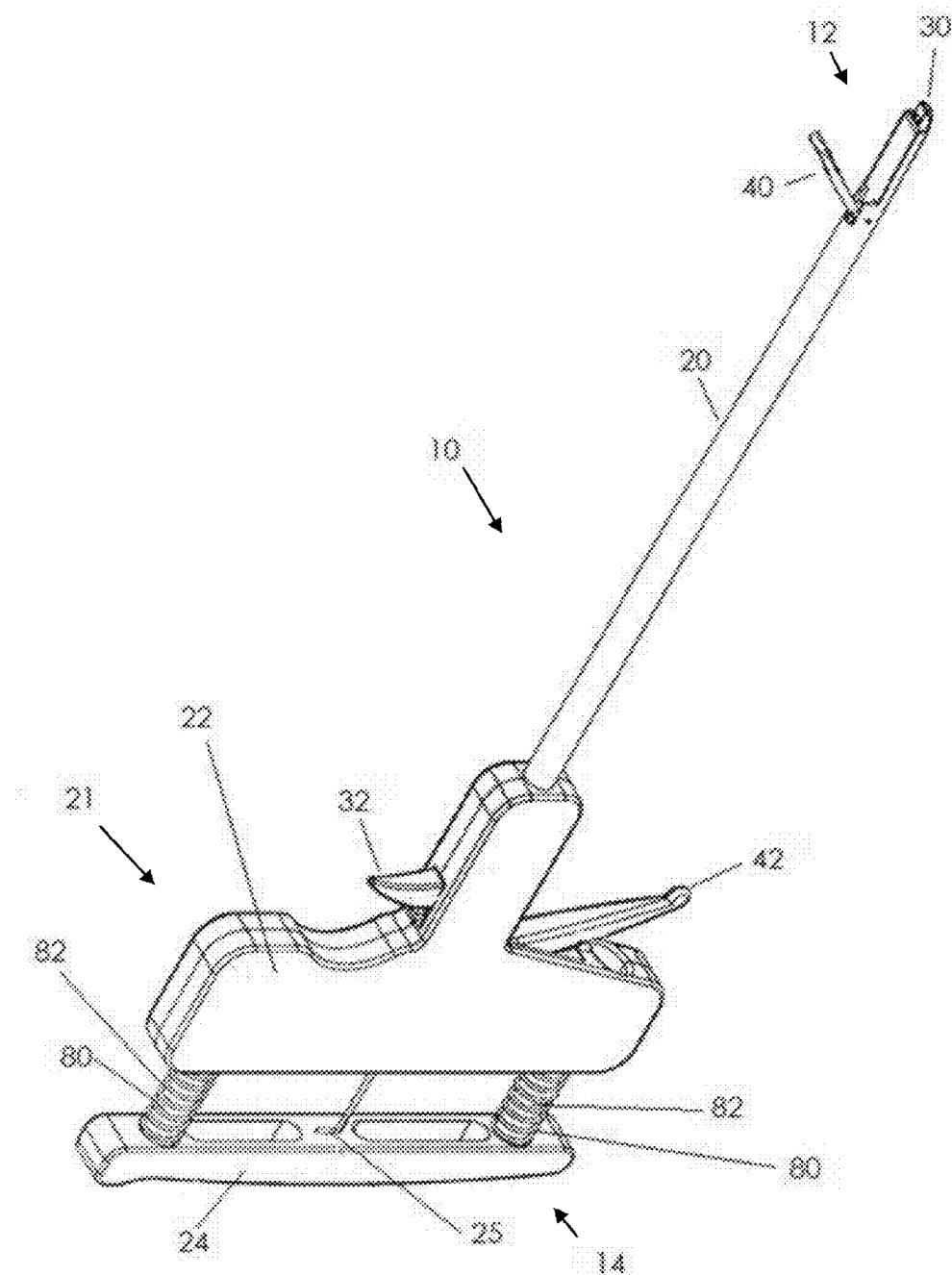
FIG. 1 is a perspective view of the suture passer device of the present invention with a top view in an open position.
Figure 1B:
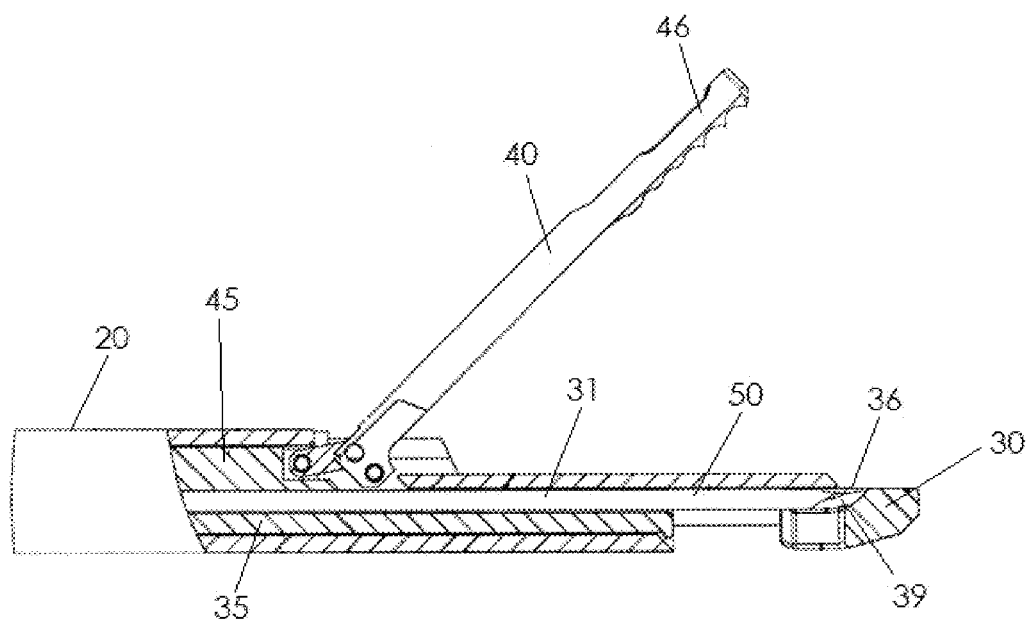
FIG. 1B is an enlarged cross-sectional view of the tip end take from FIG. 1A.
Figure 1C:
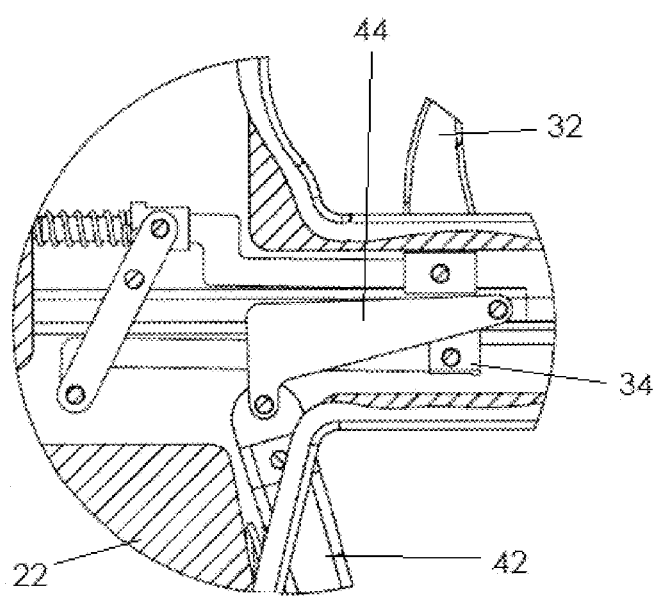
FIG. 1C is cross-sectional view of a portion of the handle taken from FIG. 1A.

FIG. 1 is a perspective view of the suture passer device 10 of the present invention. The device 10 has a handle assembly 21 at a proximal end 14 made in two parts, a main fixed handle portion 22 and a proximal movable handle portion 24 spaced by two alignment pins 80 and held open by springs 82. A tubular shaft 20 is rigidly fixed to the main handle portion 22. As illustrated, with a top perspective view, device 10 is in an open position and at the distal end 12, there is a closing top jaw clamp 40 that is controlled by the bottom first trigger mechanism 42 which when pulled closes the top jaw clamp 40. The top second trigger mechanism 32, when pulled back, opens a bottom suture hook 30, when both triggers 32, 42 are squeezed, as seen in FIG. 1. FIG. 1B is a cross sectional view of a portion taken from FIG. 1A. FIG. 1A shows the linkages 34, 44 with regards to their control of each shaft 35, 45 which runs through the tubular shaft 20 and controls the top jaw clamp 40 and lower suture hook 30. The shaft 35 and the lower suture hook 30 is a solid piece that goes all the way through the tubular shaft 20 and the proximal end of the shaft 20 connects directly to the linkage 44 which connects to the top second trigger 32. FIG. 1D shows a view of the portion of the movable handle portion 24 attachment taken from FIG. 1A. FIG. 1D shows a handle alignment pin 80 and the rear movable handle portion 24 connected to the two alignment pins 80 and springs 82 held in the front main handle portion 22 of the assembly 21. The alignment pins 80 and springs 82 and part 83 are the way in which the rear movable handle portion 24 slides towards the front main handle portion 22 and there a suture passer needle 50 rests in a slot 25 in the rear movable handle portion 24. The disposable needle 50 moves by squeezing the rear handle portion 24 in toward the front handle portion 22 so that needle 50 is pushed through an opening 31 in the hook shaft 35 and upward by the sloped groove 39 at a closed end of the opening 36 through an opening 46 in the closed jaw clamp 40.

Figure 2:
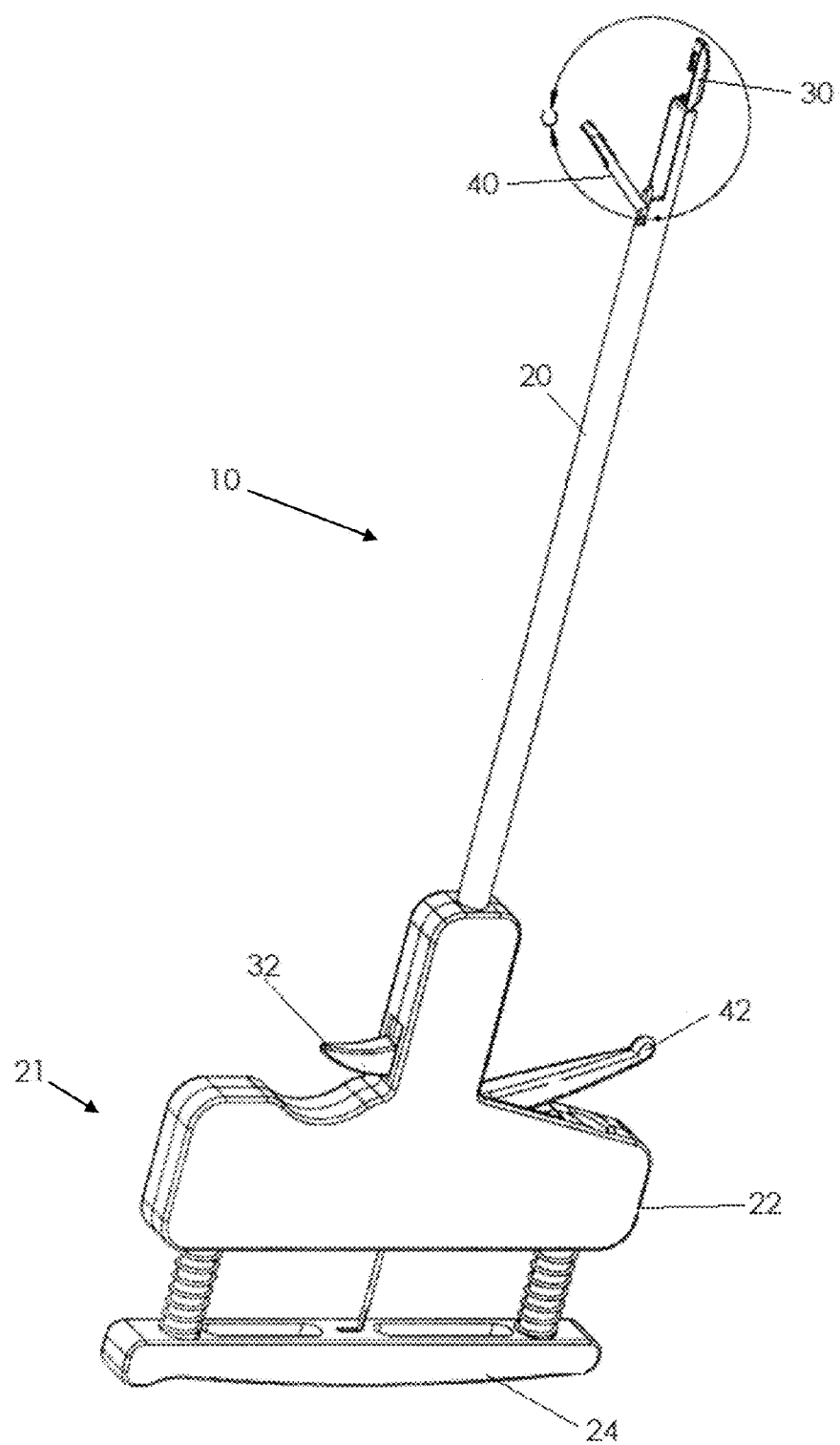
FIG. 2 is a perspective view of the suture passer device of the present invention showing the tip end with the suture hook in an open position.

FIG. 2 is a perspective of the suture passer device 10 of the present invention shown with the suture hook in the open position. This occurs when the top second trigger 32 has been pulled.

As shown in FIG. 3A, the suture hook 30 has a slotted opening 36 into which a suture 100 can be snagged and pulled into the closed end sloped groove 39 inside the distal end 23 of the hook 30.

Figure 3:
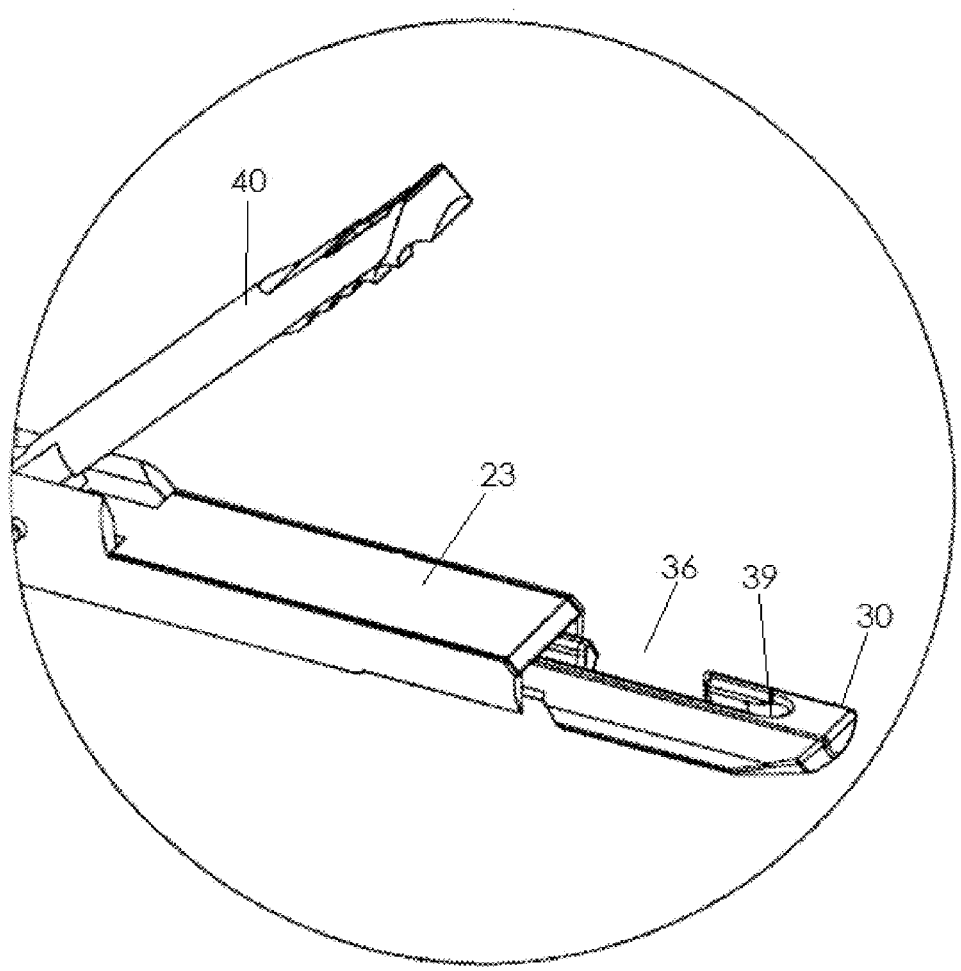
FIG. 3 is an enlarged view of the tip end shown in FIG. 2.

FIG. 3 is an enlarged view of the tip end shown in FIG. 2. It shows the hook being open with the distal end 23 placed over the needle 50 which prevents or stops the needle 50 from protruding too early.

Figure 4:
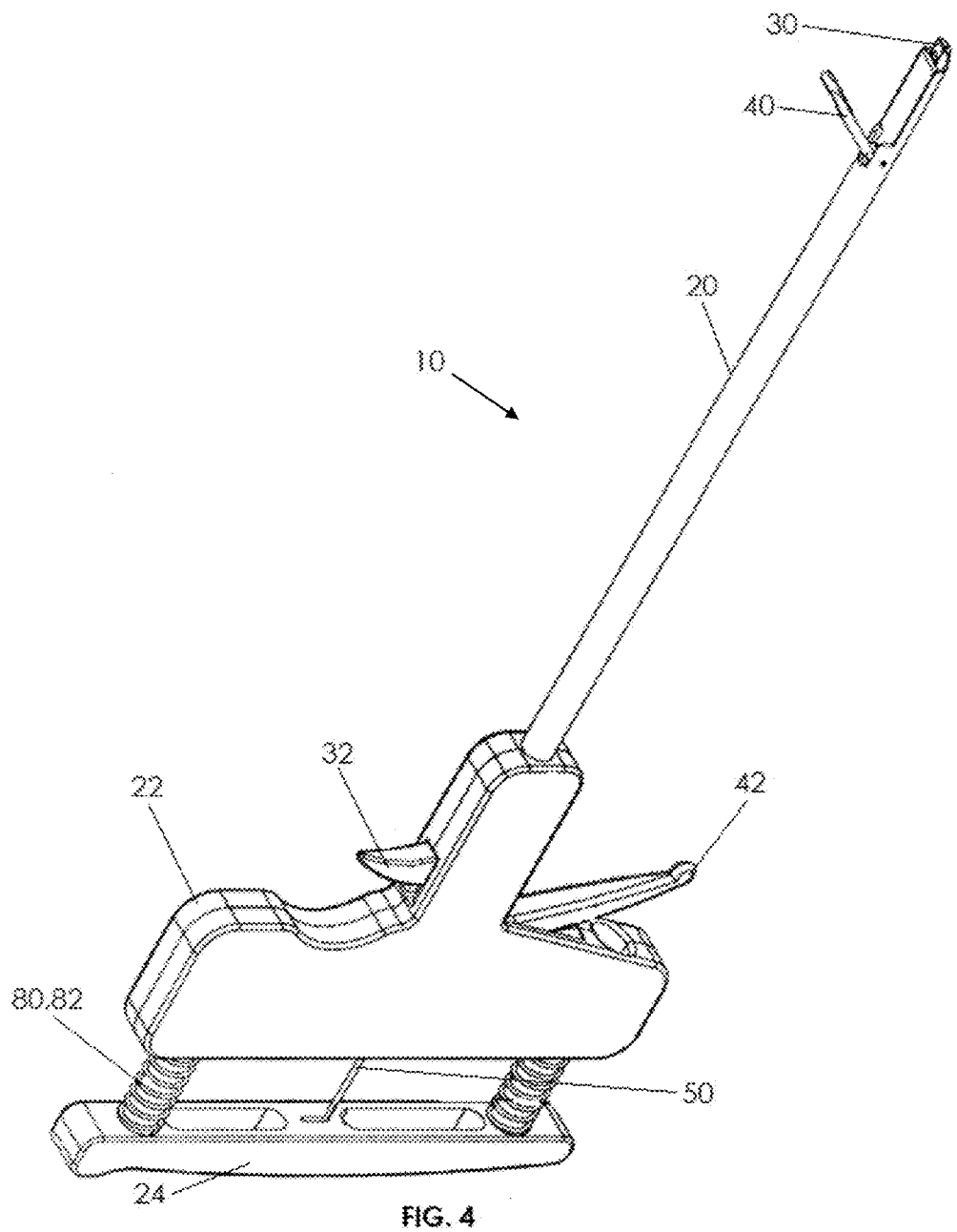
FIG. 4 is a perspective view of the suture passer device of the present invention showing the suture hook in a retracted condition.

FIG. 4 is a perspective view of the suture passer device 10 of the present invention showing the suture hook 30 in a retracted condition. This occurs when releasing the top second trigger 32, it forces the hook 30 to retract back into the tube shaft 20.

Figure 5:
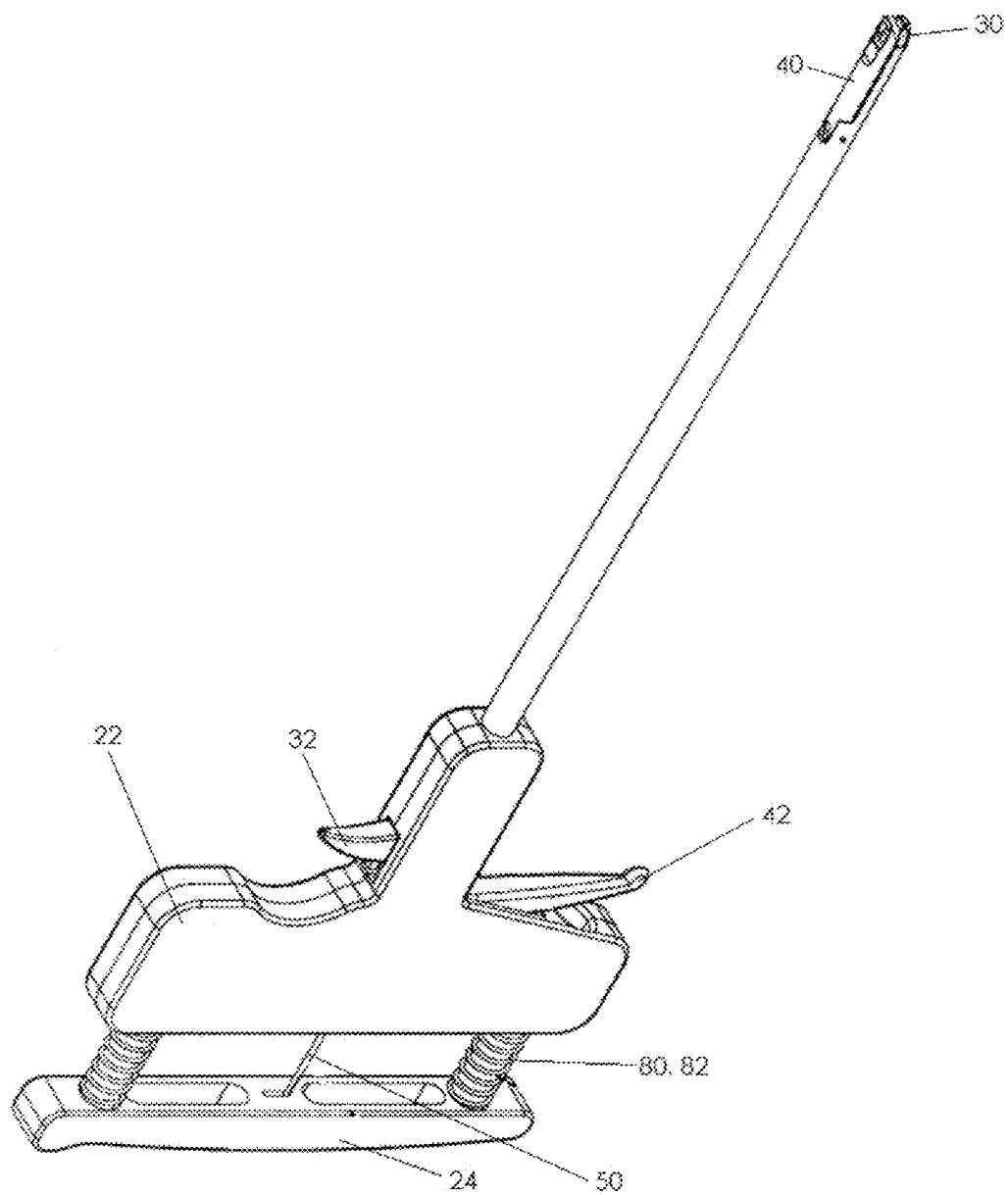
FIG. 5 is a perspective view of the suture passer device of the present invention showing the top view moved in a closed position.

FIG. 5 is a perspective view of the suture passer device 10 of the present invention showing the top view moved in a closed position. That would be when the bottom first trigger 42 is pulled, the bottom first trigger 42 connects to a link 44 which then forces the shaft 45 forward toward the distal end closing the top jaw clamp 40.

Figure 6:
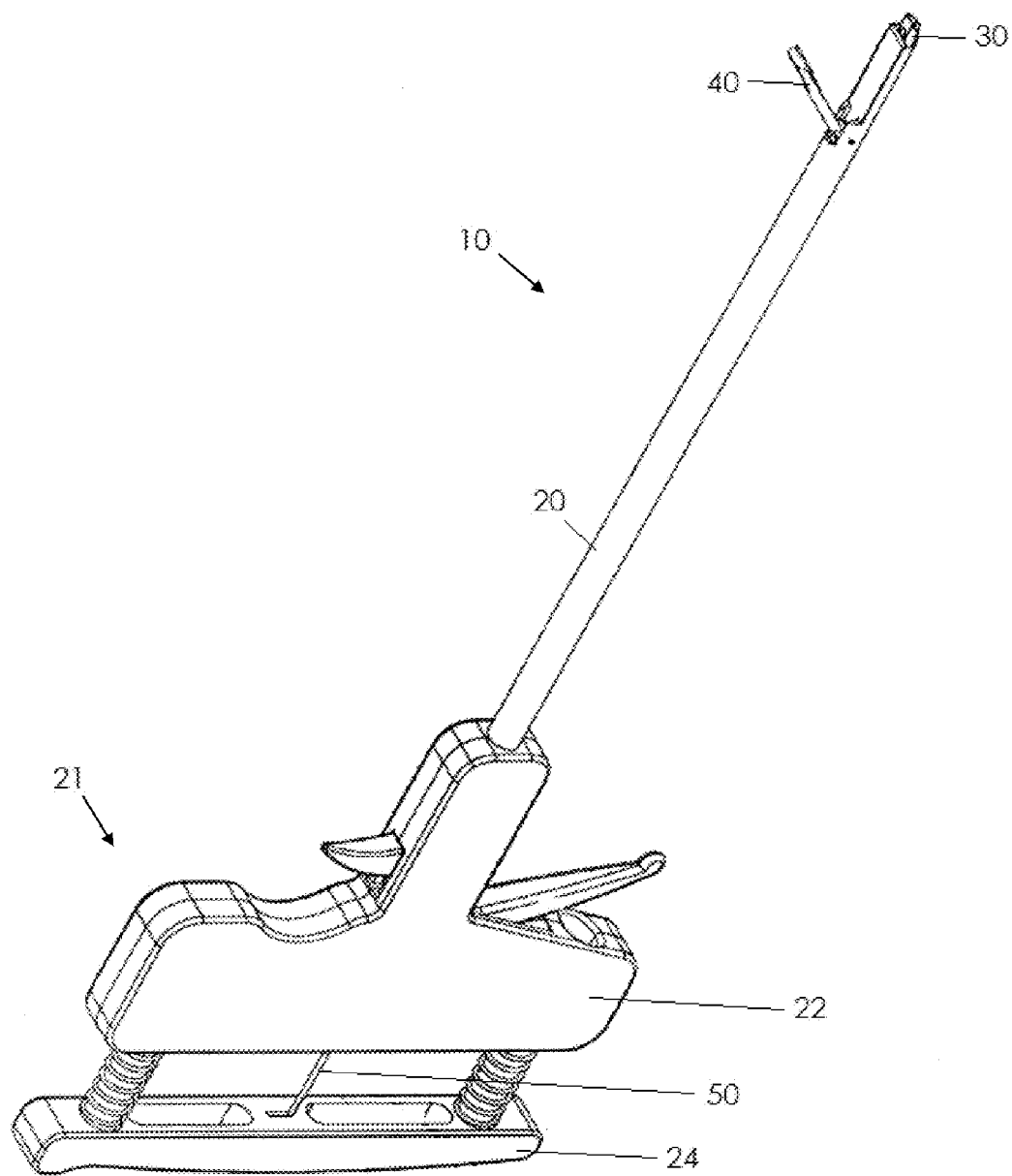
FIG. 6 is a perspective view of the suture passer device of the present invention with the top jaw open and the suture hook retracted as a starting position or step.

FIG. 6 is a perspective view of the suture passer device 10 of the present invention with the top jaw clamp 40 open and the suture hook 30 retracted as a starting position or initial step. This is where the suture is not yet being pressed or pulled and is just a position the device 10 would be in normally held there by the triggers and linkages.

Figure 7:
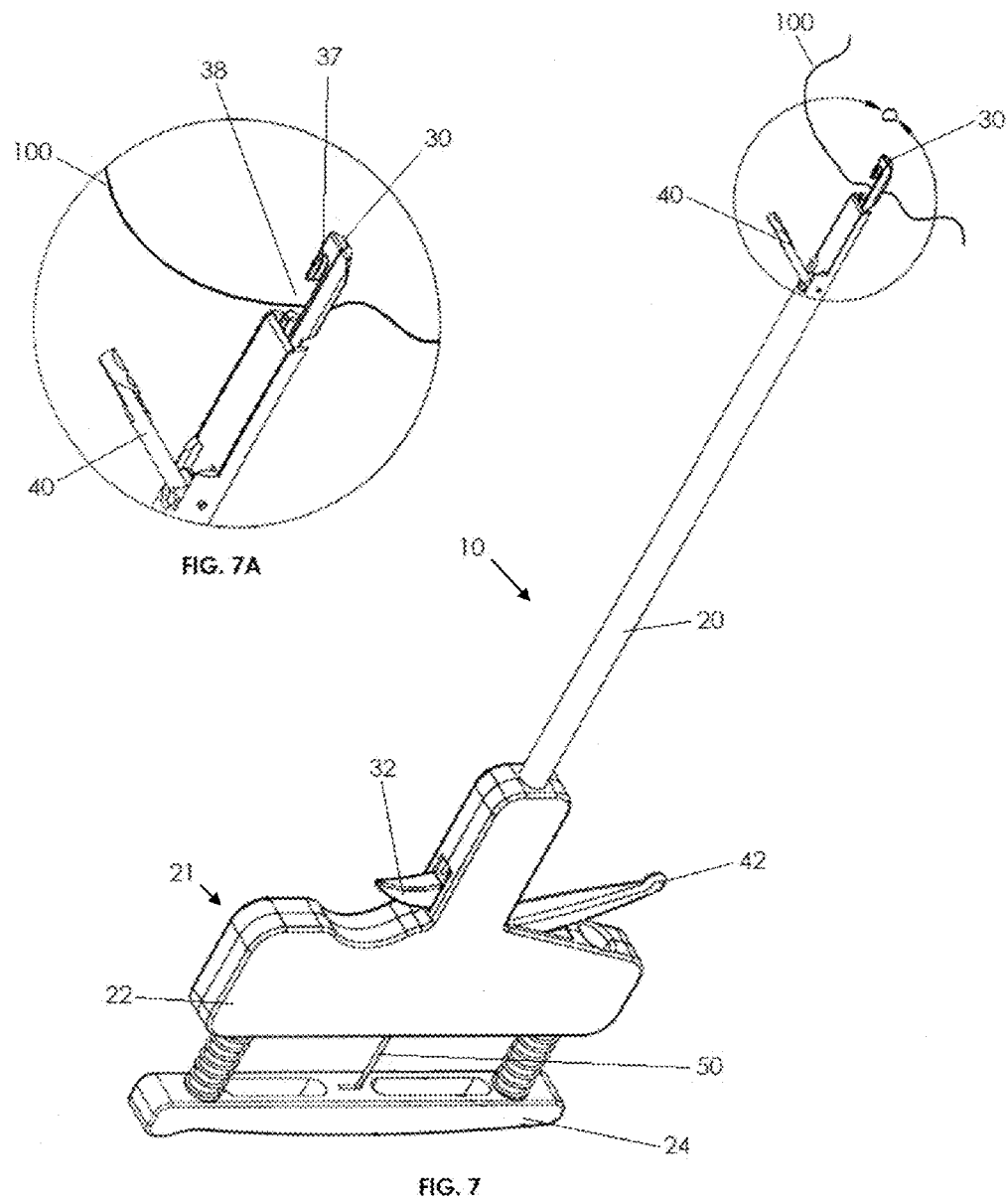
FIG. 7 is a perspective view of the suture passer device of the present invention shown with the top jaw open and the suture hook extended to hook a suture as a second position or step.
Figure 13:
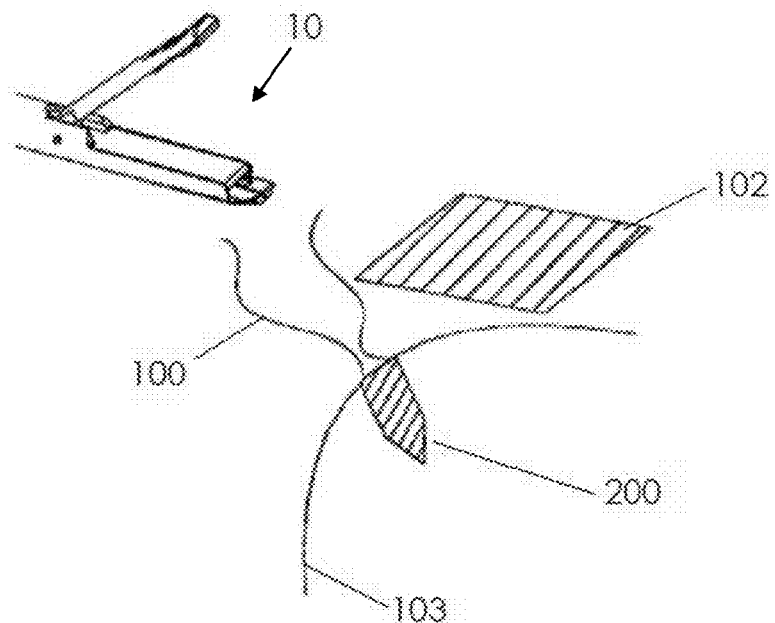
FIG. 13 shows the device with an anchored suture secured to a bone anchor in a bone and tissue, schematically shown in a cross hatched parallelogram, above the bone.

FIG. 7 is a perspective view of the suture passer device 10 of the present invention shown with the top jaw clamp 40 open and the suture hook 30 extended to hook a suture 100 as a second position or step. This is after a surgeon has the top jaw of the distal end of the device 10 enter the body of a patient and there is suture 100 already attached to a suture anchor 200, as shown in FIG. 13, already in place and by pulling the top second trigger 32 opens and extends the bottom suture hook 30. The bottom suture hook 30 then extends out where the suture 100 can be hooked using that open slot of the hook 30 and when released from inside the tubular shaft 20. The suture 100 is then held within a small groove 39 of the closed slot end of opening 36 of the suture hook 30.

FIG. 7A shows this in enlarged view of the tip end taken from FIG. 7.

Figure 8:
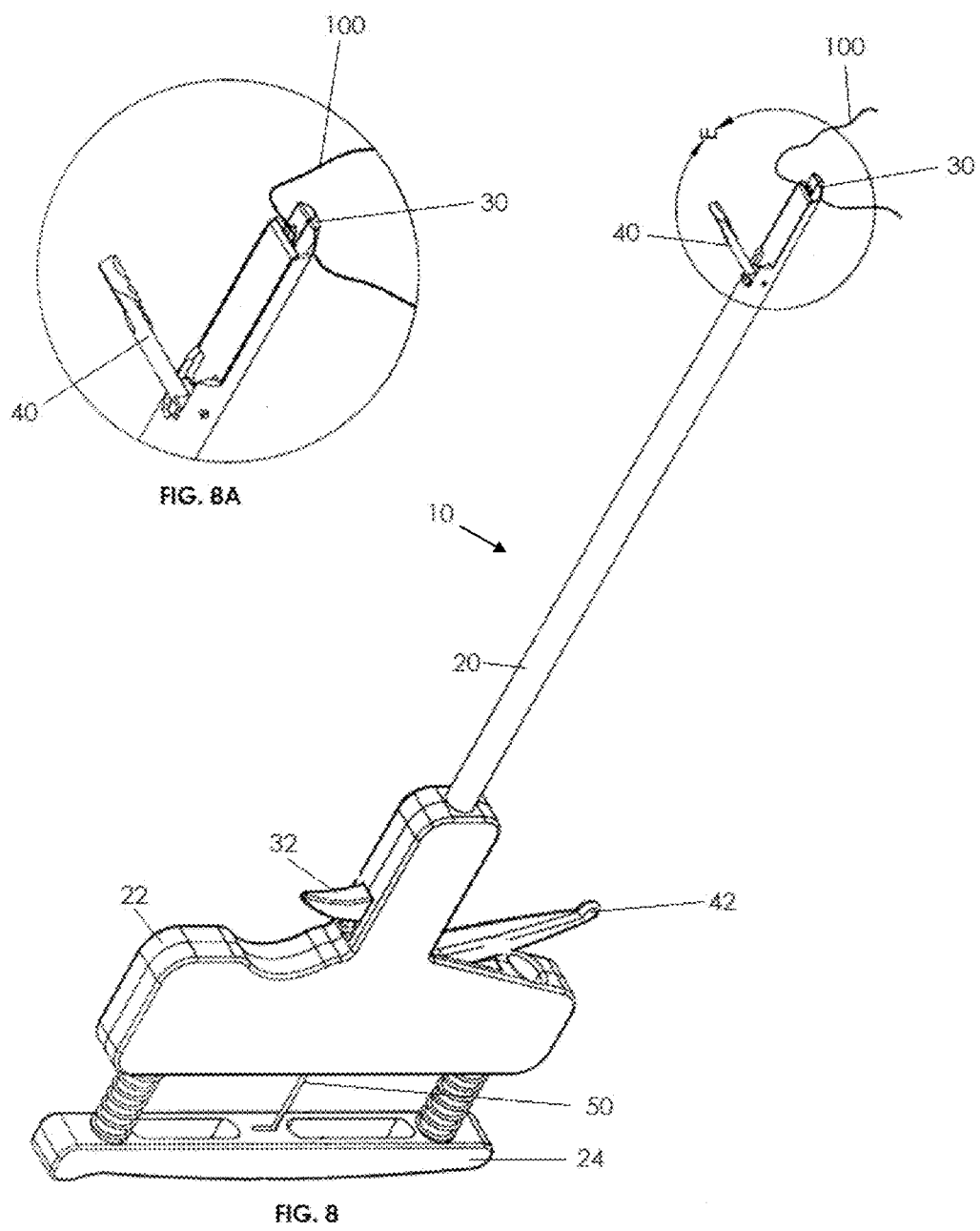
FIG. 8 is a perspective view of the suture passer device of the present invention showing the jaw open, but the suture hook with a suture in a retracted position as a third position or step.

FIG. 8 is a perspective view of the suture passer device 10 of the present invention showing the jaw clamp 40 open, but the suture hook 30 with a suture 100 in a retracted position as a third position or step. This is when the top second trigger 32 is released and a spring inside the first handle 22 causes the lower hook shaft 35 to retract back within the tubular shaft 20 and the suture 100 then sits within the small groove in the hook shank shaft 35.

FIG. 8A a larger view of the tip end taken from FIG. 8.

Figure 9:
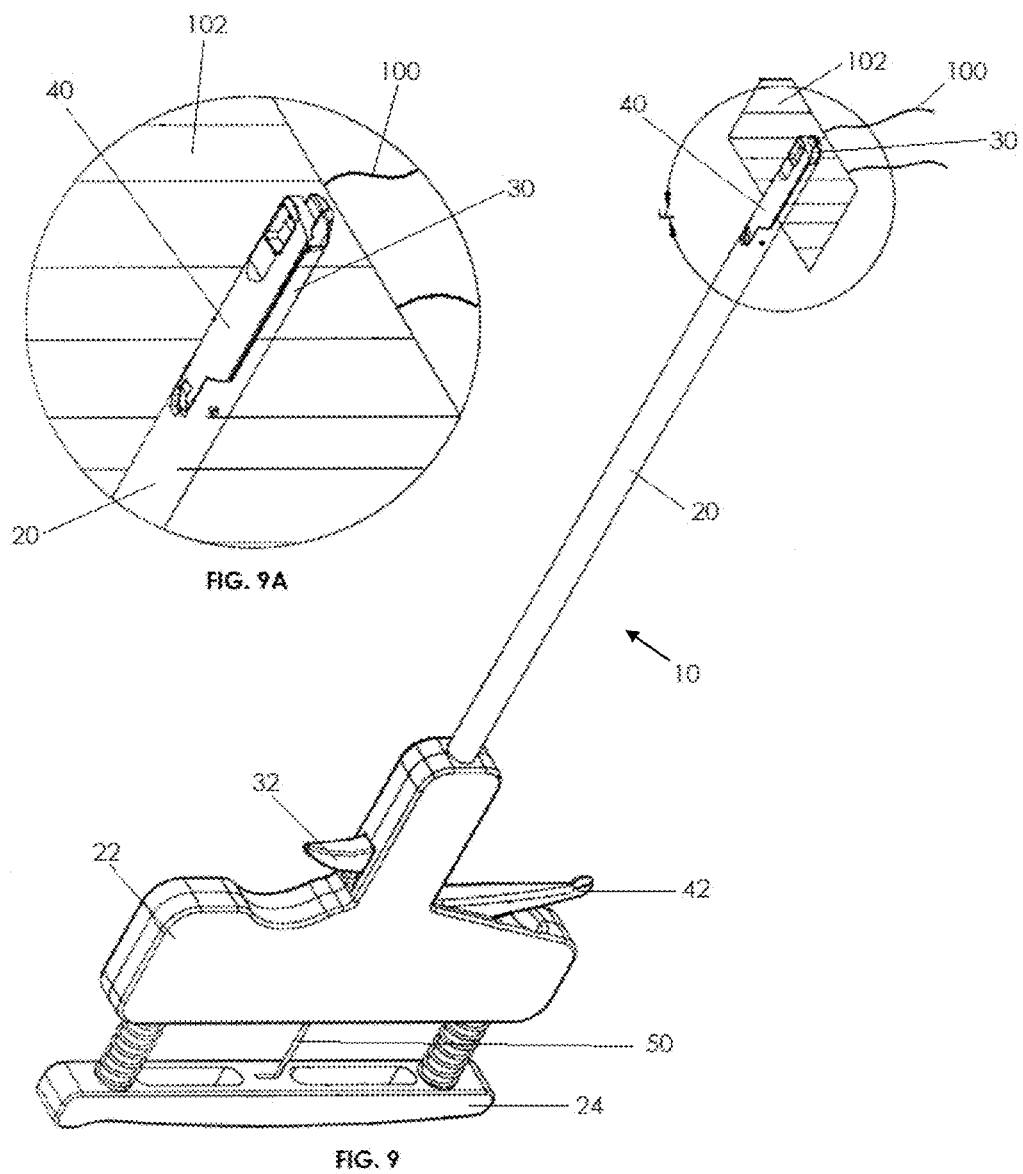
FIG. 9 is a perspective view of the suture passer device of the present invention showing the top jaw in a closed position with the tip end embedded in tissue with a suture held in the device as a fourth position or step.

FIG. 9 is a perspective view of the suture passer device 10 of the present invention showing the top jaw clamp 40 in a closed position with the tip end embedded in tissue 102 with a suture 100 held in the device 10 as a fourth position or step. This step is after the suture 100 has been hooked and the suture hook 30 is retracted back into the tubular shaft 20. The surgeon can then squeeze the bottom first trigger 42 lowering the top jaw down onto the tissue clamping it between the lower portion of the tube and the top jaw clamp 40. At this step, the suture 100 has been hooked within the lower suture hook 30 and the top jaw clamp 40 is closed on top of the tissue 102 and bottom of the tubular shaft 20 with the hook 30 is below the tissue 102.

FIG. 9A is an enlarged view of the tip end embedded in tissue 102 taken from FIG. 9.

Figure 10:
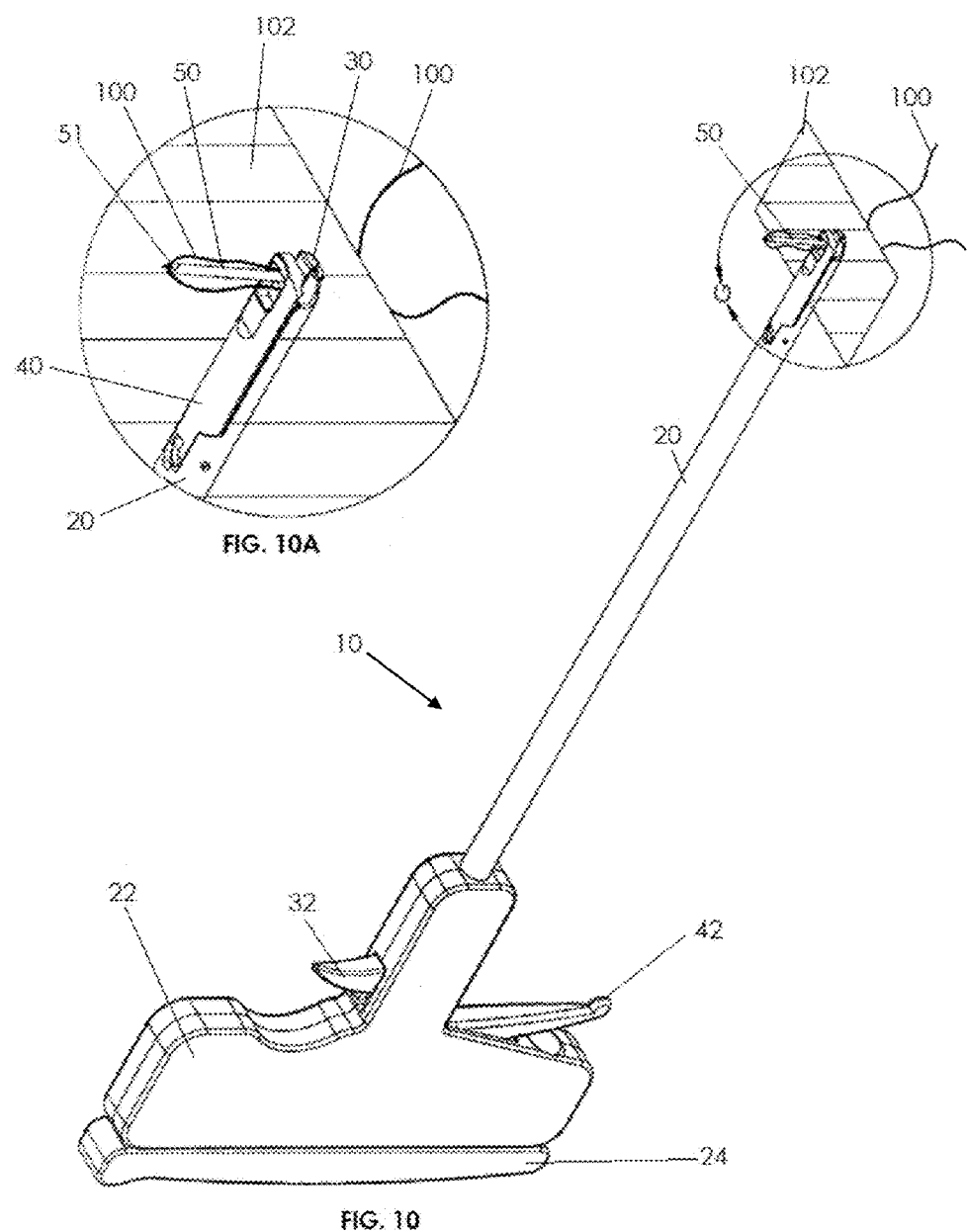
FIG. 10 is a perspective view of the suture passer device of the present invention with the needle projected out of the tip end transverse to an opening in the top jaw pushing the suture into the tissue to form a loop as a fifth position or step.

FIG. 10 is a perspective view of the suture passer device 10 of the present invention with the needle 50 projected out of the tip end transverse to an opening 46 in the top jaw clamp 40 pushing the suture 100 into the tissue 102 to form a loop 104 as a fifth position or step. After the top jaw clamp 40 and bottom shaft portion 20 and hook 30 are on either side of their respective portions of the tissue 102. The rear movable handle 24 is squeezed while the bottom first trigger 42 is still being pulled. The rear movable handle 24 pushes the needle 50 to be held in place as the rear handle is kept squeezed closed. The needle 50 is pushed forward through the hollow tubular shaft 20 and channel which lies in the shaft 35 of the hook 30. The needle 50 is pushed up through that groove or through channel and out through the opening 46 of the top jaw clamp 40 and carries the suture 100 through the tissue 102 with it just by capturing the suture 100 in a cup or concave end 51 of the needle 50.

FIG. 10A shows an enlarged view of the needle 50 passing through the top jaw clamp 40 holding the suture 100 in this end 51.

Figure 11:
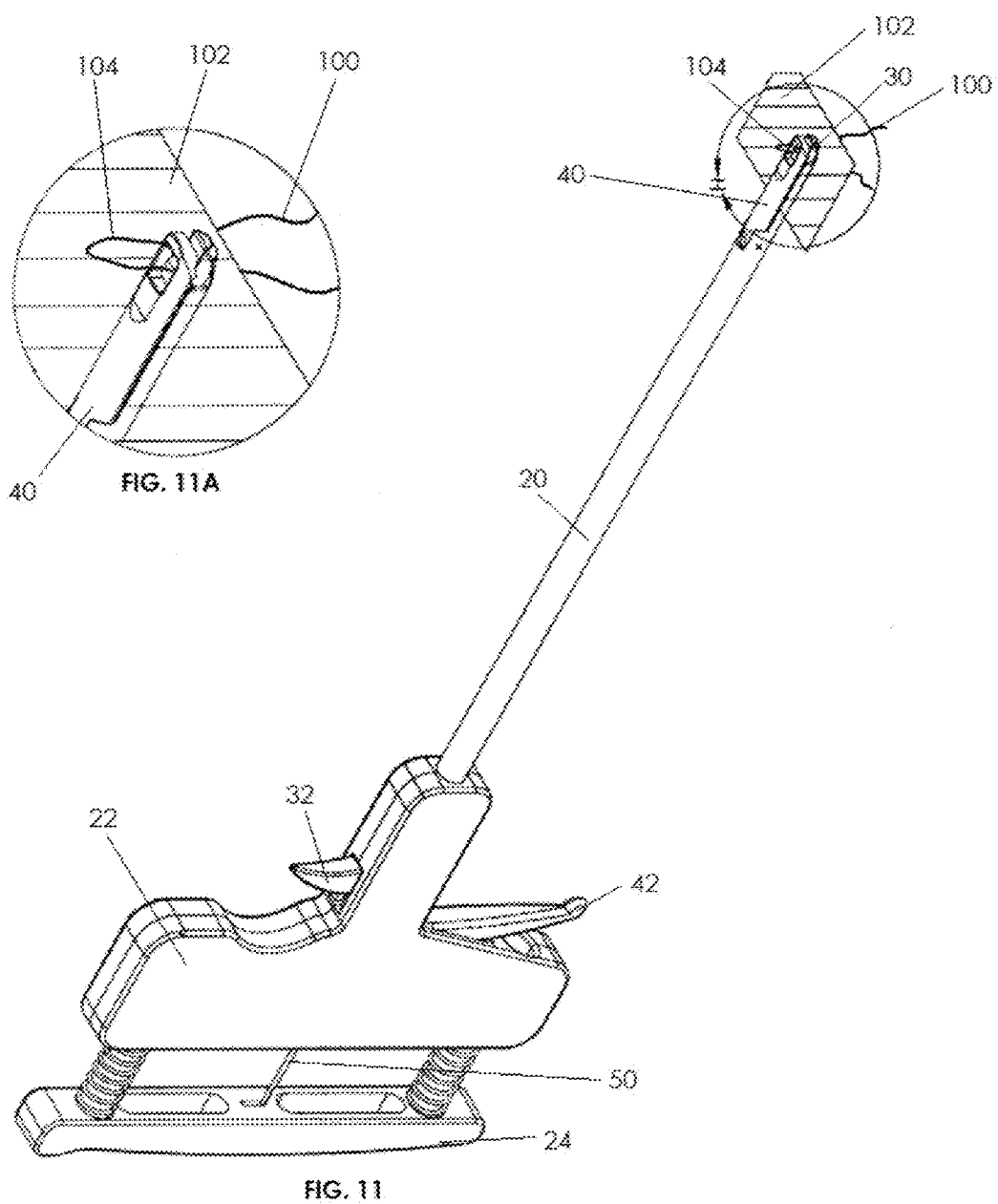
FIG. 11 is a perspective view of the suture passer device of the present invention showing the needle retracted back into the tip end leaving a suture loop in the tissue as a sixth position or step.

FIG. 11 is a perspective view of the suture passer device 10 of the present invention showing the needle 50 retracted back into the distal tip end leaving a suture loop 104 in the tissue 102 as a sixth position or step. This is when the rear movable handle 24 is released and the springs 82 force it backwards. The needle 50 which is held in a channel or slot 35 of the rear handle 24 pulls the needle 50 as the rear handle 24 is released the needle 50 retracts back within the hollow tubular shaft 20 leaving the suture 100 proud of the tissue 100 at a top of the device 10 entry opening just leaving a loop 104 within the tissue. The suture 100 is released by extending the suture hook 30 past and unhooking the suture 100.

FIG. 11A shows an enlarged view of the suture 100 being held in place when the needle 50 is retracted.

Figure 12:
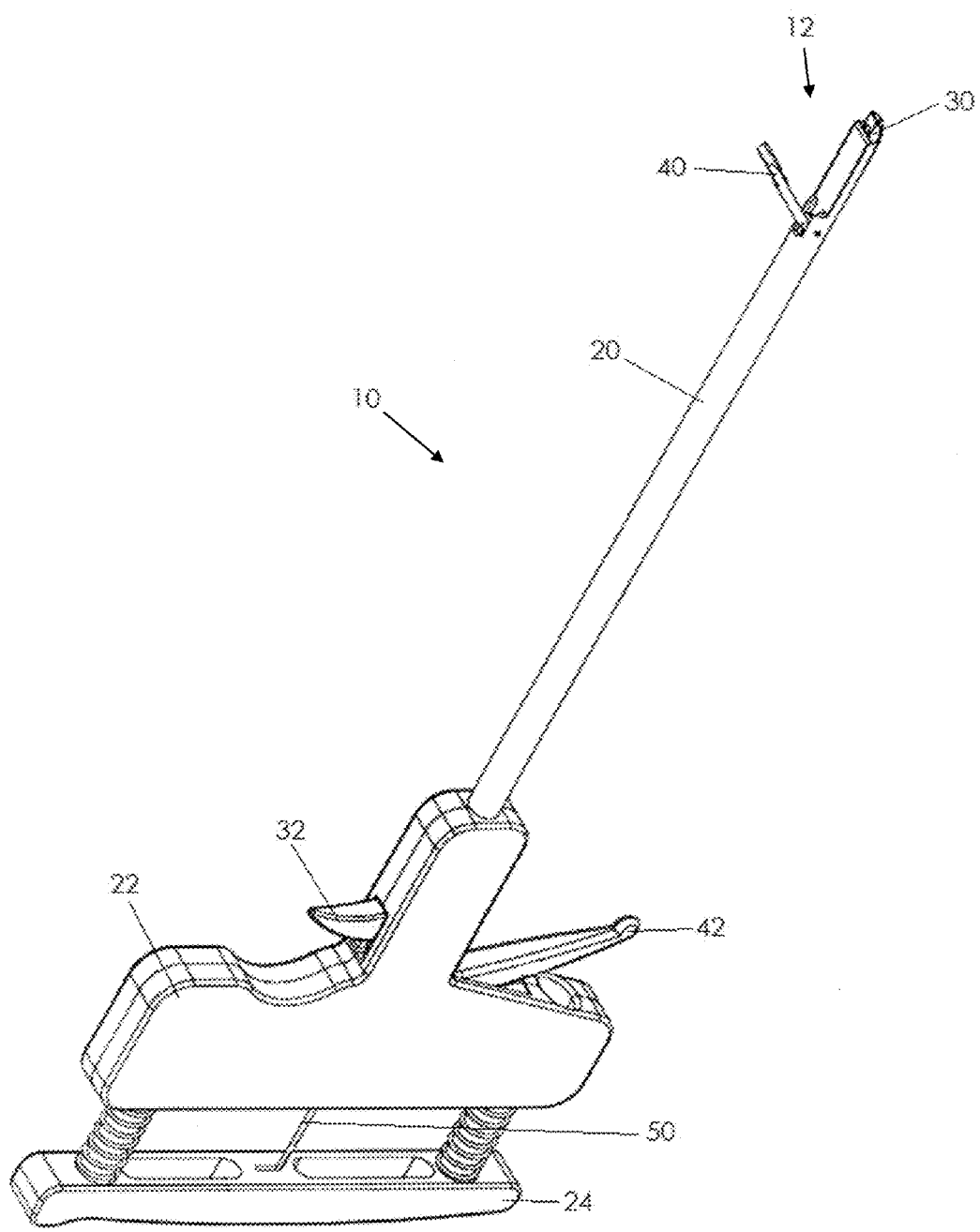
FIG. 12 is a perspective view of the suture passer device of the present invention with the device shown at a final position or step with the suture released.

FIG. 12 is a perspective view of the suture passer device 10 of the present invention with the device 10 shown at a final position or step with the suture 100 released. FIG. 12 shows after all processes have been completed and the bottom first trigger 42 is released again it returns to its resting state where the top jaw clamp 40 remains open. The process allows the surgeon to now repeat the cycle again for however many sutures remain. After each return pass they can always pull simultaneously through a spinal cannula if so desired.

Once the loop 104 is formed and the needle 50 is retracted, the suture 100 is released from the device 10 so you don't continue pulling suture 100 outwardly as one retracts the device 10 from the patient. As shown, the suture 100 in FIG. 11 is held in the hook 30 and the top jaw clamp 40, it is just a loop 104, so one can release the bottom trigger which opens up the top jaw clamp 40 and it's no longer a part of the suture 100/tissue 102 equation and then one would pull on the top second trigger 32, as the next step to open the suture hook 30 to extend the hook 30 and release it from the sutures 100 or open it off the sutures. As one pulls away from the sutures 100, the suture loops 104 remain in the tissue 102.

The suture hook 30 has to be put in an extended position to fully release the suture 100. The device 10 can be put it on a slight angle or the end pushed it slightly forward so it goes into the opening so the suture 100 can be fully released. One simply has to pull the top second trigger 32 so that it opens the suture hook 30 and then slide it slightly forward and to the side of the suture 100 so that the sutures 100 are released. The same way the surgeon grabbed it initially is how he would just reverse the process to release the suture loop 104.

Figure 13A:
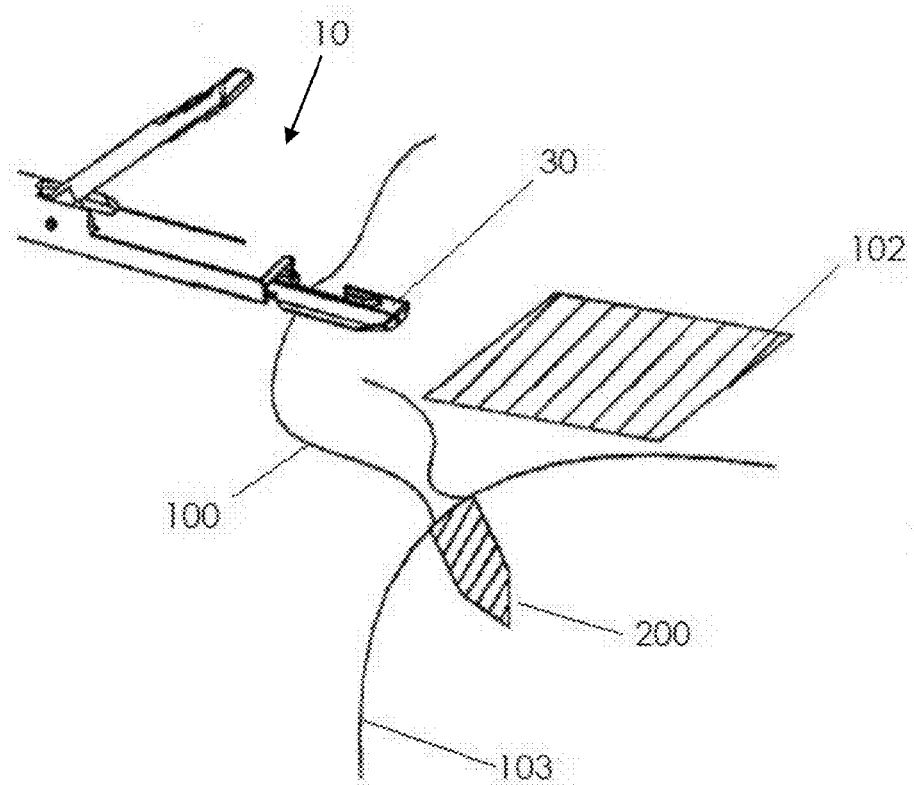
FIG. 13A-13H show schematically the steps using the device to create the suture loops.
Figure 13B:
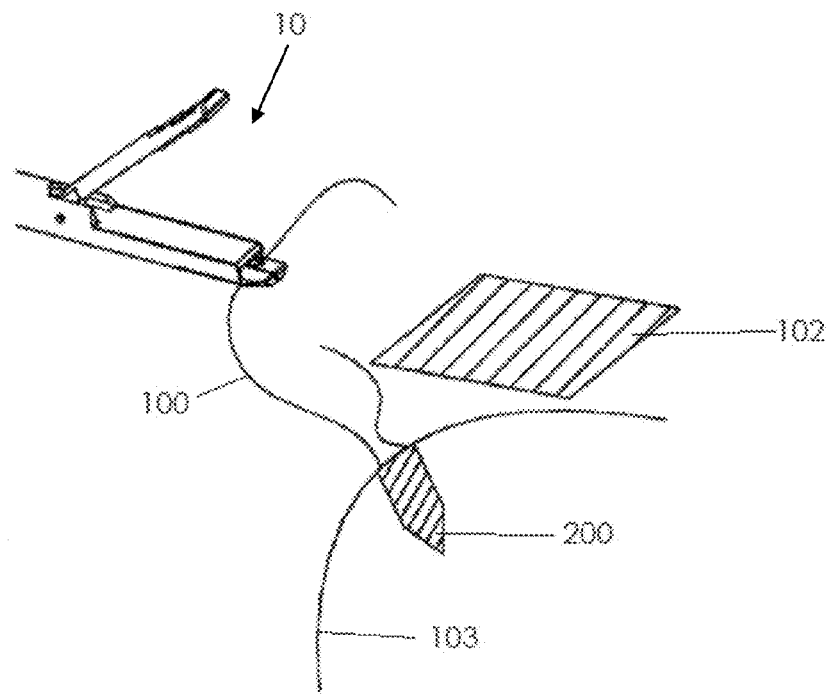
Figure 13C:
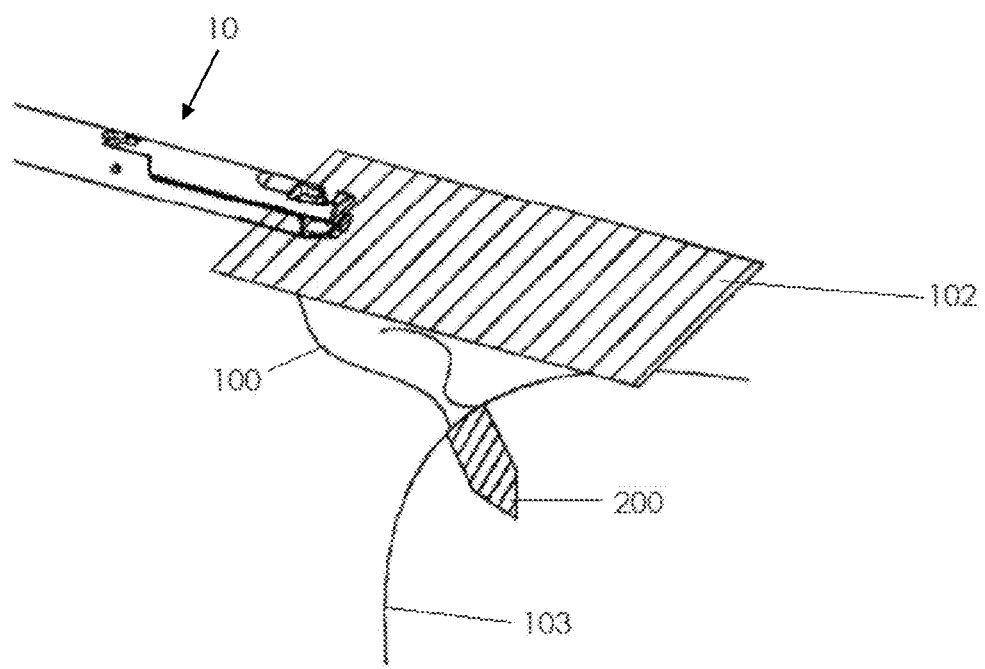
Figure 13D:
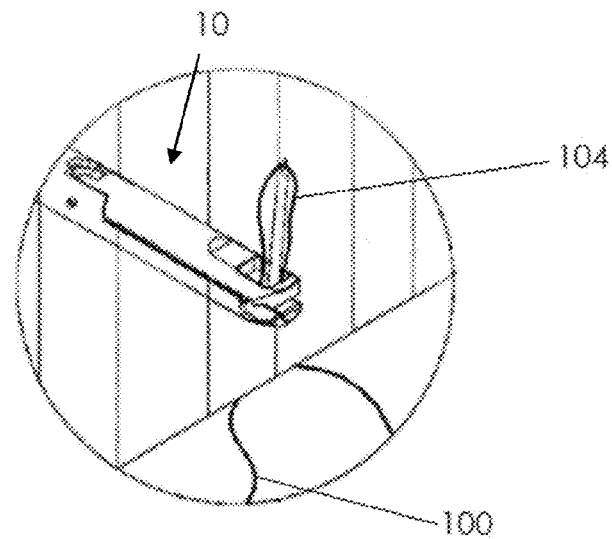
Figure 13E:
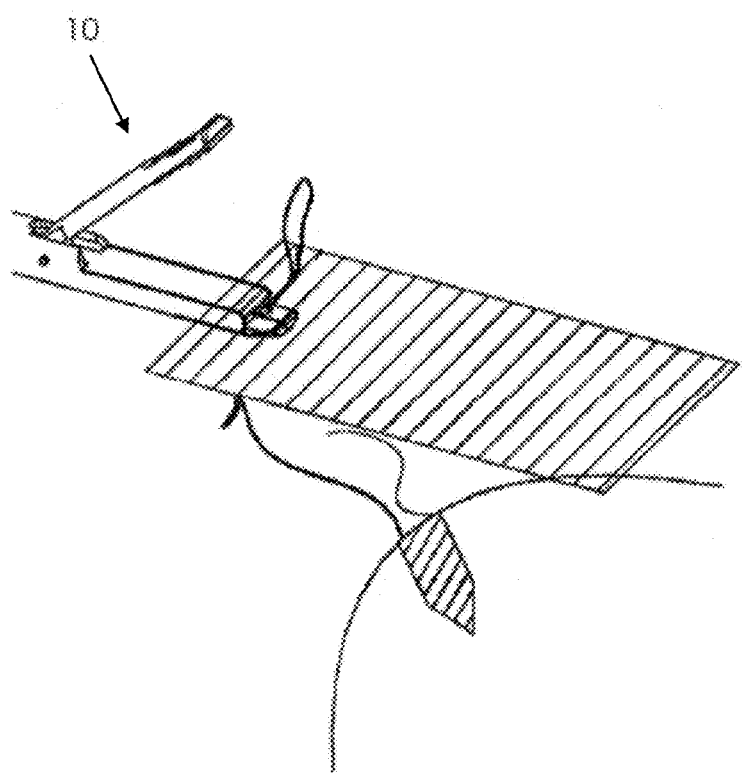
Figure 13F:
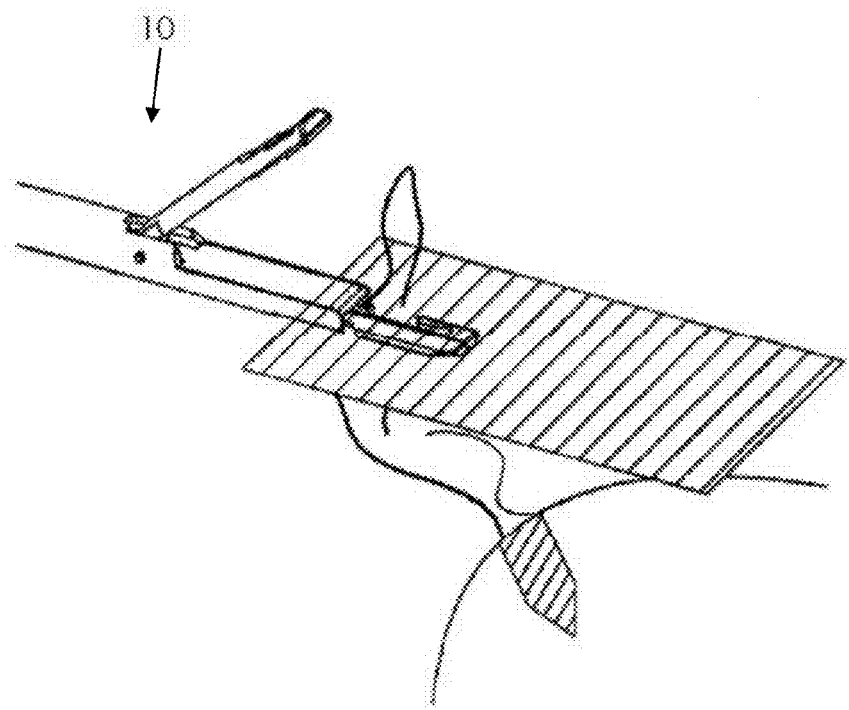
Figure 13G:
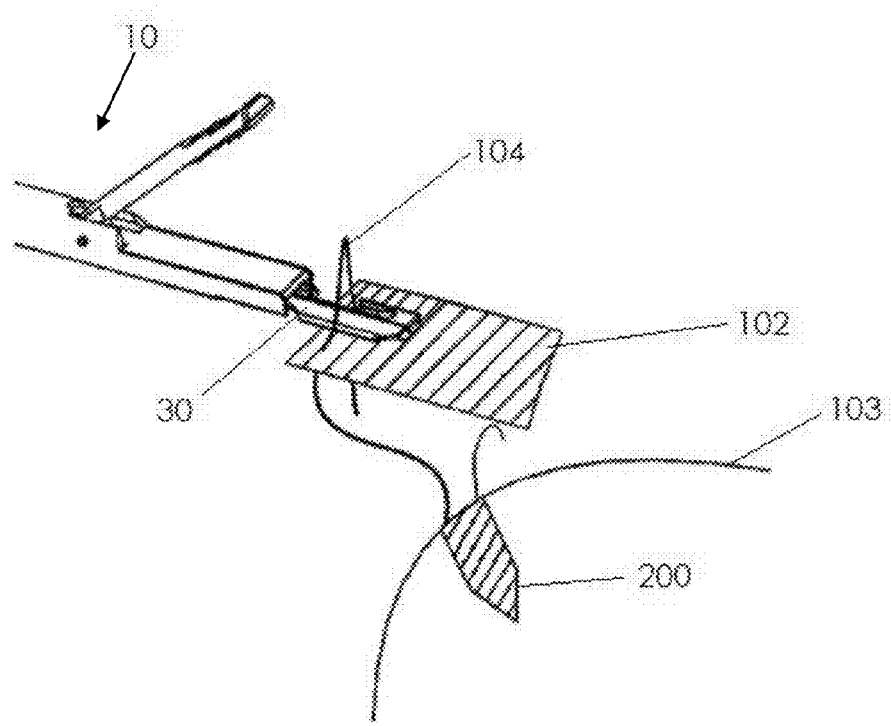
Figure 13H:
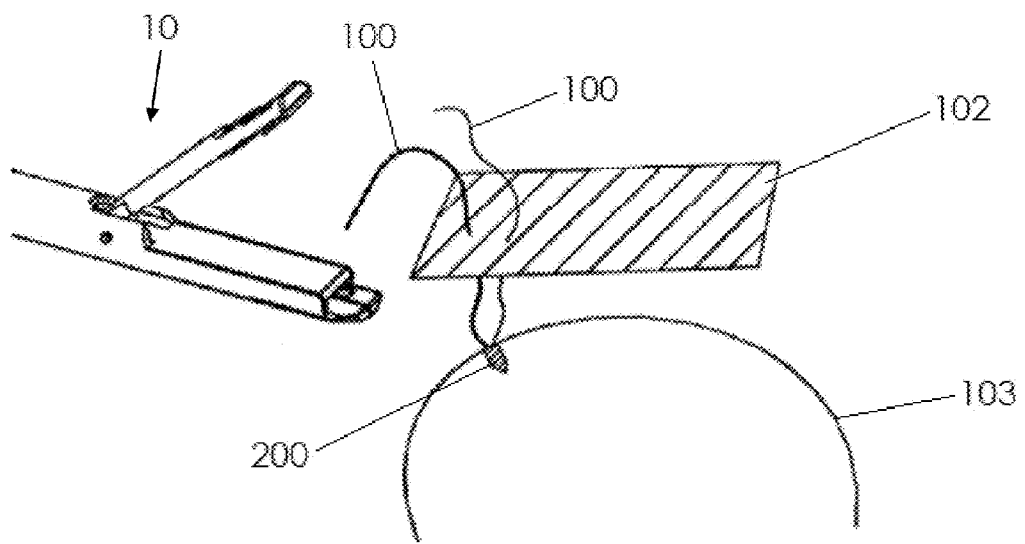

FIG. 13 shows the device 10 with an anchored suture 100 secured to a bone anchor 200 in a bone 103 and tissue 102 above the bone 103. FIGS. 13A-13H show the steps of using the device 10 to create the suture loops 104. In FIG. 13A the suture hook 30 is contacting an anchored suture 100 end. FIG. 13B shows retracting the suture hook 30 with a single suture 100 in the channel 39. The step with the suture in the suture hook 30, clamp the top jaw clamp 40 on the top of the tissue 102 using the bottom first trigger 42 and the flat portion of the hollow tube under the tissue 102, is shown in FIG. 13C. In FIG. 13D, the needle 50 is shown pushing the suture 100 through the tissue 102 by compressing the movable handle portion 24. With the suture 100 pushed through the tissue 102, the bottom first trigger 42 is released to open the top jaw clamp 40, as shown in FIG. 13E. FIG. 3F shows opening the suture hook 30 using the top second trigger and sliding the suture passer device 10 sideways off the suture 100. These steps can be repeated for any remaining sutures 100 remaining attached to suture anchors 200. FIG. 13G shows using the extended suture hook 30 to retrieve the loose end of a suture loop 104. This step can be repeated on all passed sutures 100. In FIG. 13H, once all the sutures 100 have been passed and pulled through the tissue 102, a knot may be tied to anchor the tissue 102 back to the bone 103.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A suture passer device for creating a suture loop in tissue comprises:
    a movable jaw clamp, movable from an open position to a closed clamping position;
    a tubular shaft with a proximal end and a distal end and a length, the distal end for capturing a suture;
    a retractable hook movable longitudinally along the length of the tubular shaft at the distal end;
    a handle having a fixed handle portion and a movable handle portion, the handle having a first trigger mechanism connected to the movable jaw clamp by a linkage, wherein activation by retraction of the first trigger mechanism moves the movable jaw clamp to the closed clamping position and a second trigger mechanism connected to the retractable hook by a linkage, wherein activation by retraction of the second trigger mechanism extends the retractable hook external of the tubular shaft to allow capturing a suture in an opening of the retractable hook;
    a needle attached to the movable handle portion and positioned internal of the fixed handle and the tubular shaft; and
    wherein when the movable handle portion closes, the needle is bent passing through a distal opening transverse to the tubular shaft, the needle having a concave end to hold and push a suture through the tissue and form a loop in the tissue, releasing the movable handle retracts the needle back within the tubular shaft leaving the suture loop proud within the tissue.

2. A suture passer device for creating a suture loop in tissue comprises:
    a handle having a fixed handle portion and a movable handle portion;
    a tubular shaft with a proximal end and a distal end and a length, the distal end for capturing a suture;
    a needle attached to the movable handle portion and positioned internal of the fixed handle and the tubular shaft;
    a retractable hook movable longitudinally along the length of the tubular shaft at the distal end;
    a first trigger mechanism connected to a movable jaw clamp by a linkage, wherein activation by retraction of the first trigger mechanism moves the movable jaw clamp to a closed clamping position;
    a second trigger mechanism connected to the retractable hook by a linkage, wherein activation by retraction of the second trigger mechanism extends the retractable hook external of the tubular shaft to allow capturing a suture in an opening of the retractable hook; and
    wherein when the movable handle portion closes, the needle is bent passing through a distal opening transverse to the tubular shaft, the needle having an end to hold a suture and form a loop in the tissue.

3. The suture passer device of claim 2 further comprises:
    the movable jaw clamp, movable from an open position to a closed clamping position.

4. A suture passer device for creating a suture loop in tissue comprises:
    a handle assembly, the handle assembly having a first trigger mechanism, a second trigger mechanism and a movable proximal handle portion attached to a fixed handle portion biased to an open position by one or more springs;
    a tubular shaft with a proximal end and a distal end;
    a movable jaw clamp, movable from an open to a closed clamping position by the activation of the first trigger mechanism;

a retractable hook movable by activation of the second trigger mechanism;

a suture passer needle connected to the movable proximal handle and stowed inside the tubular shaft; and wherein the suture passer device captures a suture by an extension of the retractable hook, retraction bringing the suture into the tubular shaft, closing the jaw clamp captures tissue, compressing the movable handle portion moves the needle outward of the distal end directionally transverse to the tubular shaft through an opening in the movable jaw clamp as a concave end of the needle holds and pushes the suture moving the suture through the tissue to create a suture loop in tissue, releasing the movable handle retracts the needle back within the tubular shaft leaving the suture loop proud within the tissue.

5. The suture passer device of claim 4 wherein the handle further comprises:

the first trigger mechanism connected to the movable jaw clamp by a linkage, wherein activation by retraction of the first trigger mechanism moves the movable jaw clamp to the closed clamping position.

6. The suture passer device of claim 4 wherein the second trigger mechanism connected to the retractable hook by a linkage, wherein activation by refraction of the second trigger mechanism extends the retractable hook external of the tubular shaft to allow capturing a suture in an opening of the retractable hook.

7. A method of creating one or more suture loops in tissue comprises the steps of:

providing a suture passer device having a handle assembly, the handle assembly having a first trigger mechanism, a second trigger mechanism and a movable proximal handle portion attached to a fixed handle portion biased to an open position by one or more springs; a tubular shaft; a movable jaw clamp, movable from an open to a closed clamping position by the activation of the first trigger mechanism; a retractable hook movable by activation of the second trigger mechanism; a suture passer needle connected to the movable proximal handle and stowed inside the tubular shaft;

extending the retractable hook by activating the second trigger mechanism;

capturing a suture in an opening or slot of the extended retractable hook;

retracting the retractable hook;

clamping the movable jaw clamp to position tissue between the captured suture and the movable jaw clamp by activating the first trigger mechanism; and compressing the movable handle portion to move the needle through an opening in the movable jaw clamp as an end of the needle holds the suture and the needle is bent directionally transverse to the tubular shaft and the end penetrates through the tissue past the closed movable jaw clamp to form a suture loop.

8. The method of claim 7 repeating the steps of claim 7 one or more times to create multiple suture loops.

9. The method of claim 8 further comprises:

passing an end of the suture or separated sutures through the loop to secure it to the tissue.

10. The method of claim 7 further comprises:

passing an end of the suture or a second suture through the loop to secure it to tissue.

* * * * *